(12) United States Patent
Shatos et al.

(10) Patent No.: US 7,316,927 B2
(45) Date of Patent: Jan. 8, 2008

(54) CULTURE OF GOBLET CELLS

(75) Inventors: Marie A. Shatos, Athol, MA (US);
Darlene A. Dartt, Newton, MA (US);
Jose D. Rios, Woburn, MA (US)

(73) Assignee: The Schepens Eye Research Institute, Inc., Boston, MA (US)

(*) Notice: Subject to any disclaimer, the term of this patent is extended or adjusted under 35 U.S.C. 154(b) by 0 days.

(21) Appl. No.: 11/441,890

(22) Filed: May 26, 2006

(65) Prior Publication Data

US 2007/0092965 A1  Apr. 26, 2007

Related U.S. Application Data

(62) Division of application No. 10/398,574, filed as application No. PCT/US01/31485 on Oct. 5, 2001, now Pat. No. 7,052,690.

(60) Provisional application No. 60/238,220, filed on Oct. 5, 2000.

(51) Int. Cl.
*C12N 5/08* (2006.01)
*C12N 5/00* (2006.01)
*A61K 35/42* (2006.01)

(52) U.S. Cl. ............... 435/366; 435/325; 435/371; 424/93.7; 424/571; 424/572; 424/574

(58) Field of Classification Search ............ 424/93.7, 424/571, 572, 574; 435/325, 366, 371
See application file for complete search history.

(56) References Cited

U.S. PATENT DOCUMENTS 5,872,215 A * 2/1999 Osbourne et al. ........ 530/387.3

OTHER PUBLICATIONS

Lancaster et al., "Goblet cell carcinoid arising in a mature teratoma of the mediastinum", Am J Surg Pathology, Jan. 1997, 21(1):109-13, abstract.*
Shrestha et al., "Immunohistochemical, ultrastructural and molecular study of well differentiated adenocarcinomas of the lung predominantly composed of goblet cells", Lung Cancer, Nov. 1998, 22(2):103-17, abstract.*
Hughes et al., "Gastric mucous neck cell and intestinal goblet cell phenotypes in gastric adenocarcinoma", J Clim Pathology, 1997, 50:741-748.*

* cited by examiner

*Primary Examiner*—Ruth A Davis
(74) *Attorney, Agent, or Firm*—Weingarten, Schurgin, Gagnebin & Lebovici LLP

(57) ABSTRACT

The invention encompasses isolation, culture and characterization of goblet cells in vitro from mammalian conjuctiva. Goblet cells can be cultured from conjunctiva of such mammals as, e.g., humans, rats, mice, rabbits and the like. In another aspect of the invention, the culture of goblet cells has a concentration of pure goblet cells of 10% or greater. In a further embodiment, the invention comprises an immortalized goblet cell line.

6 Claims, 19 Drawing Sheets

Human Goblet Cells can be Grown in Culture

Phase Microscopy

Cultured Human Goblet Cells are Negative for Cytokeratin 4

Cultured Human Goblet Cells are Positive for HPA and Cytokeratin 7

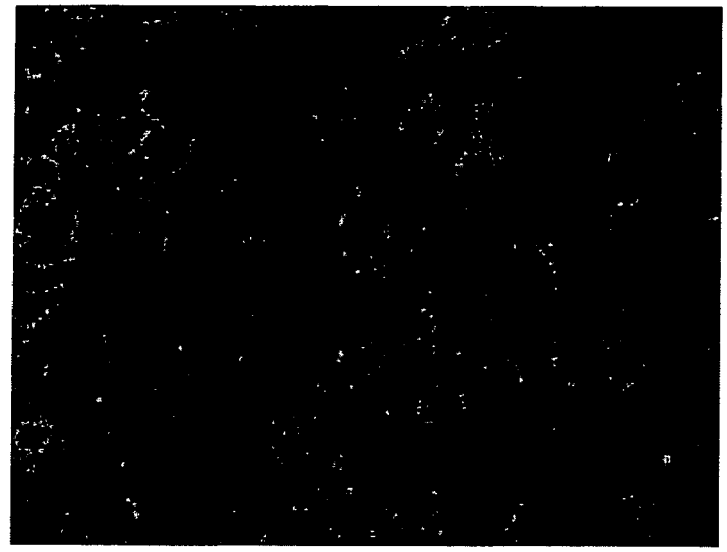
FIG. 18B
FIG. 18A

Cultured Human Goblet Cells are Positive for MUC5AC

CULTURE OF GOBLET CELLS

CROSS REFERENCE TO RELATED APPLICATIONS

This present application is a divisional application of U.S. application Ser. No. 10/398,574 which was filed on Apr. 7, 2003 now U.S. Pat. No. 7,052,690 entitled CULTURE OF GOBLET CELLS which a 35 U.S.C. §371 filing of International Application No. PCT/US01/31485 was internationally filed on Oct. 5, 2001 and which further claims the priority of U.S. Provisional Application No. 60/238,220, filed on Oct. 5, 2000, the whole of which are each hereby incorporated by reference herein.

STATEMENT REGARDING FEDERALLY SPONSORED RESEARCH OR DEVELOPMENT

The work leading to the invention received support from the United States federal government under grant no. NIH EY 09057. Therefore, the federal government may have certain rights in this invention.

BACKGROUND OF THE INVENTION

The epithelium comprising the conjunctiva is classified as a non-keratinizing stratified squamous epithelium consisting of several layers (Gipson, 1994). Goblet cells, highly specialized epithelial cells are located in the apical surface of the conjunctiva, interspersed among the layers of stratified epithelium (Wei et al.; Geggel et al.). These cells are readily identified by their extensive apical accumulation of secretory vesicles (Jeffery et al.; Huang et al.) and can occur either singly as in humans and other mammals (Kessing; Latkovic; Tseng et al.) or in clusters as found in the conjunctiva of adult rats (Srinivasan et al.). Irrespective of species, goblet cells are primarily responsible for the secretion of the inner mucous layer of the tear film, which provides a physical and chemical barrier to protect the ocular surface from dryness or other deleterious environments and/or a variety of noxious agent. (Lamberts; Nichols et al.; Gibbons; Lemp et al.) In this regard, goblet cells synthesize, store and secrete high molecular weight glycoproteins referred to as mucins, which upon secretion have the ability to hydrate and gel, producing a protective scaffolding over the ocular surface. (Chao et al.; Steuhl) Maintenance of this covering is essential to the health of the corneal and conjunctival surface. Inability or interference in the ability of goblet cells to secrete normal levels of mucin can lead to pathological abnormalities within the conjunctiva. Mucin deficiency often results as a consequence of ocular cicatricial pemphigoid, Steven Johnson syndrome, alkali burns and neurotrophic keratitis whereas overproduction of mucin due to excessive goblet cell secretion or proliferation is thought to be mediated by activated T-cells and macrophages and by a chronic conjunctivitis such as atopic keratoconjunctivitis. (Lemp, 1973; Tseng, *Ophthalmol.*, 1984; Gilbard et al.; Lemp, 1992) These diseases and their sequellae can eventually lead to deterioration of the ocular surface.

Because the importance of the goblet cell in maintaining the integrity of the ocular surface is well recognized, a large number of structural, ultrastuctural and histochemical studies have been performed on the conjunctival epithelium in a variety of species (Latkovic; Steuhl; Setzer et al.; Moore et al.; Oduntan; Breithnach et al.). Data derived from these studies have provided valuable information regarding the development, subsequent appearance, location and function of goblet cells within the conjunctiva. In addition, they have provided information concerning the influence of environmental factors, chemical, toxin and disease upon these same goblet cell parameters.

Previous reports of systems developed to culture goblet cells in vitro are limited. Goblet cell cultures derived from airway epithelia of hamsters, rats and humans (Wu et al., 1985; Kaartinen et al.; Wu et al., 1990) have been in use for several years. By comparison, the development of systems to culture conjunctival goblet cells is still in its infancy. Among the methods which have been used to study these cells include: sectioning of conjunctival tissue combined with a battery of histochemical staining; immunocytochemical localization; transmission electron microscopy and in situ hybridization (Huang et al.; Greiner et al.; Allansmith et al.; Kinoshita et al.); histochemical staining of wholemounted tissue (Huang et al.; Tseng et al., *Ophthalmol. Vis. Sci.*, 1984); PAS staining of filter paper strips applied to the conjunctival surface (Adams); phalloidin labeling of excised conjunctiva (Gipson, 1997) and neutral protease removal of viable sheets of conjunctival epithelium (Geggel et al.) and growth of conjunctival cells on various substrata including natural extracellular matrix components, fibroblast feeder layers and on collagen and matrigel (Sun et al.; Rheinwald et al.; Tsai et al.). These systems are limited in that they yield indirect information. The limitations result from the information often being extrapolated from studies using wholemounted or sectioned conjunctival tissue, or from being derived from intestinal and tracheal neoplastic cell lines, which mimic only select functions of goblet cells. Conjunctival cells have been grown from a variety of tissues including human, but no reproducible, characterized system by which goblet cells can be propagated has been reported.

Successful and consistent isolation and culture of goblet cells without altering their phenotype and/or function has been limited. In particular, normal human diploid cells have a limited proliferative lifespan in culture. In the past, it was necessary to use a variety of complex culture media as well as artificial matrices in order for the cells to attach. These techniques, however, would not always insure growth, propagation and preservation of cellular function. Therefore, there remains a need for a reliable method for culturing mammalian goblet cells.

BRIEF SUMMARY OF THE INVENTION

The present invention is directed to the isolation and subculturing conjunctival mammalian goblet cells, which exhibit morphological, histochemical, immunocytochemical, and biochemical markers indicative of goblet cells in vivo. The culture of goblet cells in accordance with the present invention provides a more effective in vitro test format, inter alia, while retaining the original phenotypic characteristics associated with goblet cells in vivo.

In an embodiment of the invention, a culture of goblet cells isolated from mammalian conjunctival tissue has a concentration of pure goblet cells of 10% or greater. Conjunctival tissue of the present invention includes the fornical region and the nictitating membrane. In particular, human goblet cells are obtained from the fornical region. The mammal of the present invention can include, inter alia, humans, rats, mice, rabbits, cats, dogs, sheeps, goats, cows, and pigs.

In a further embodiment of the invention, the concentration of goblet cells maintained in culture is preferably 10%-30%; more preferably 30%-50%, yet more preferably 50%-70%, still more preferably 70%-90%, most preferably 90%-95%, and still most preferably 95%-100%.

In another embodiment, the invention comprises a method of producing a culture of goblet cells, which has a concentration of pure goblet cells of 10% or greater. In one aspect, the method comprises providing an explant of conjunctival mammalian tissue; culturing the explant in a growth medium; allowing the explant to grow until cell growth in the form of nodules is observed around the explant; removing the explant, leaving said nodules in the growth medium; and then allowing the cells from the nodules to grow to form the culture of goblet cells. In another aspect of the method, the cells growing separately from the nodules are removed.

In another aspect of the method, the concentration of goblet cells comprised in a culture is preferably 10%-30%; more preferably 30%-50%, yet more preferably 50%-70%, still more preferably 70%-90%, most preferably 90%-95%, and still most preferably 95%-100%.

In a further aspect of the method, the conjunctival mammalian tissue comprises the fornical region and the nictitating membrane. In particular, human conjunctival tissue comprises tissue from the fornical region. In a further aspect of the method, the mammal is selected from the group consisting of human, rat, mouse, rabbit, cat, dog, sheep, goat, cow, and pig.

In a further embodiment, the invention comprises a culture of goblet cells with an extended lifespan made by the method of the present invention. In one aspect, the goblet cells of the invention are immortalized goblet cells, which are made from the method of making a culture of goblet cells of the present invention. This culture of goblet cells has a concentration of 10% or greater of pure goblet cells. In a particular aspect, the invention comprises an immortalized goblet cell line, which has a concentration of 100% goblet cells.

In yet another embodiment, the immortalized goblet cells as well as goblet cells made from the method of culturing described herein may be produced into a kit with instructions for use for examining mucin-associated effects. The kit may be used, for example, but not limited to screening various toxic compounds and consumer products, diagnosing for conditions associated with mucin deficiency, studying for allergic reactivity of various foreign substances and quantitating the amount of mucin.

In a further embodiment, the invention comprises a method of treating a patient suffering from conditions associated with conjunctival mucin deficiency. In one aspect, the method includes identifying a patient suffering from conditions associated with conjunctival mucin deficiency; providing a therapeutic composition in a pharmaceutically acceptable form for administration comprising goblet cells of the present invention; and administering to the patient a therapeutically effective amount of the composition. In a further aspect of the method of treatment, the goblet cells may be obtained from the culture of goblet cells of the invention. In another aspect, the goblet cells used to treat a patient may originate from the same patient to avoid rejection and/or deleterious autoimmune responses. In a further aspect of the method, the pharmaceutically acceptable form for administration may include, e.g., autograft transplantation, eye drops, corneal bandage, ointments, and topical treatment. In another aspect, the method includes conditions associated with conjunctival goblet cell mucin deficiency, for example, but not limited to, lacerated corneas, ocular cicatricial pemphigoid, Steven Johnson syndrome, alkali burns, and neurotrophic keratitis.

BRIEF DESCRIPTION OF THE DRAWINGS

Other features and advantages of the invention will be apparent from the following description of the preferred embodiments thereof and from the claims, taken in conjunction with the accompanying drawings, in which:

Figure 9A:
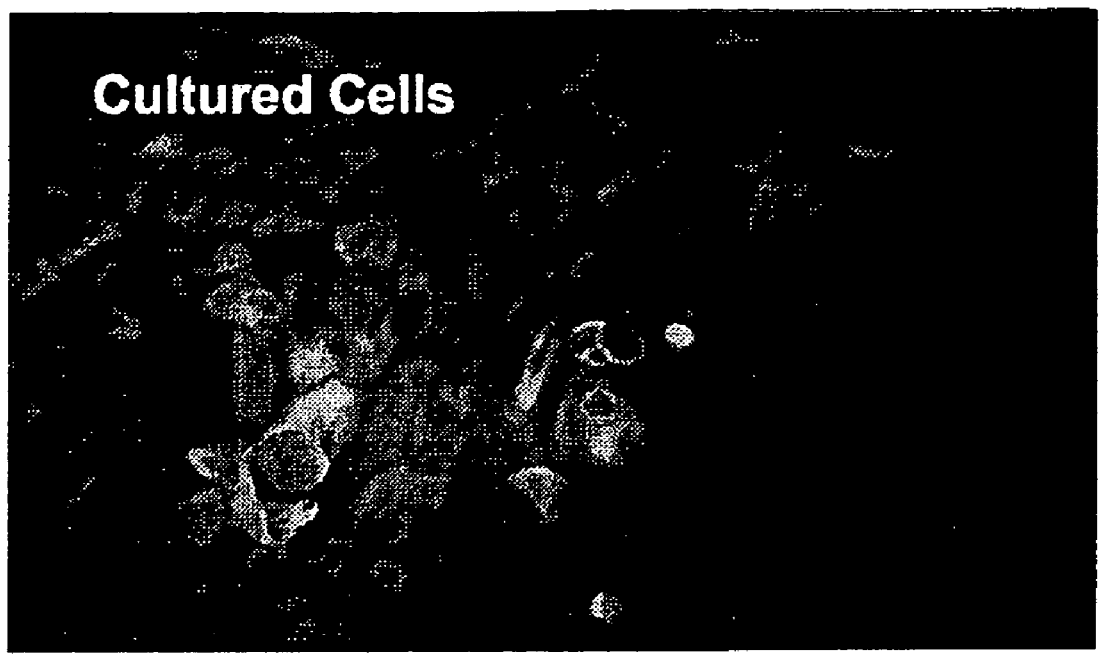
Figure 9B:
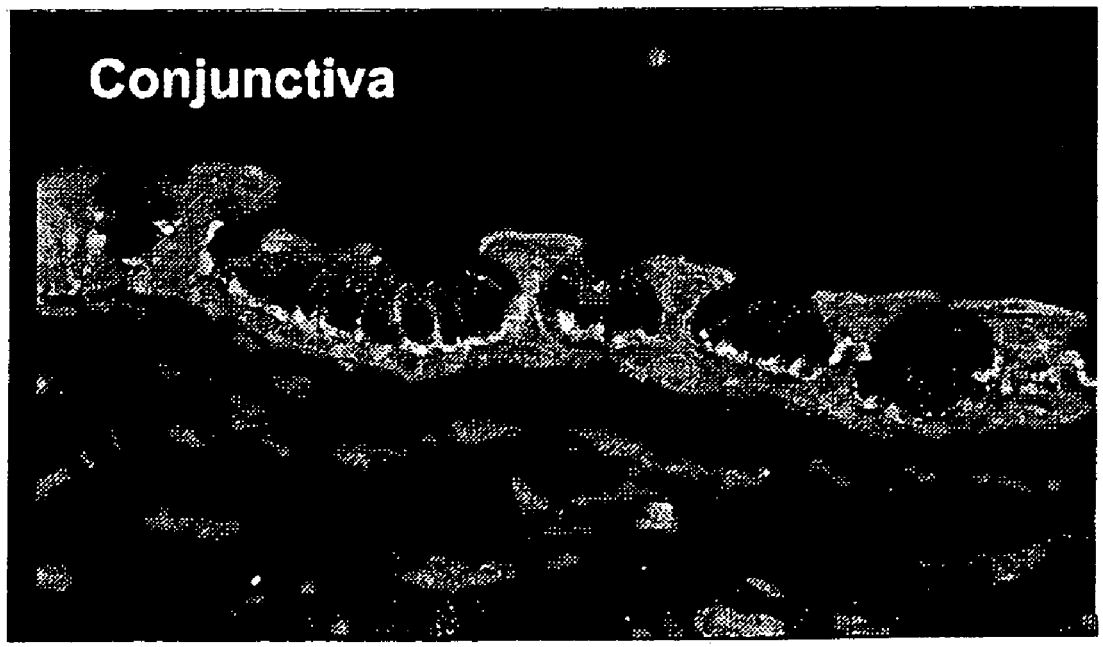
Figure 10A:
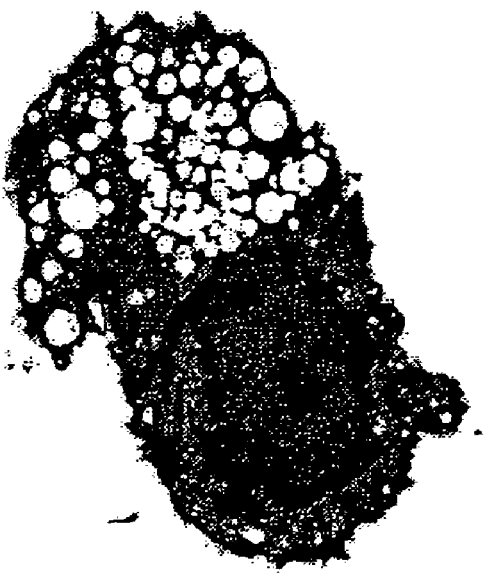
Figure 10B:
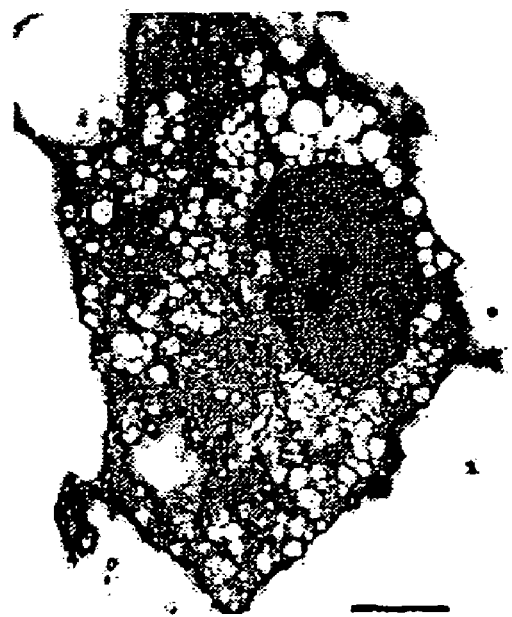
Figure 11A:
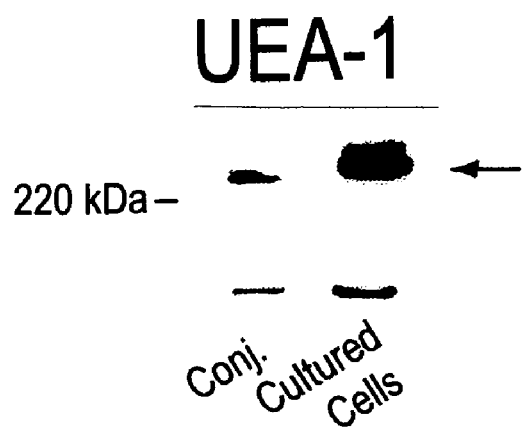
Figure 11B:
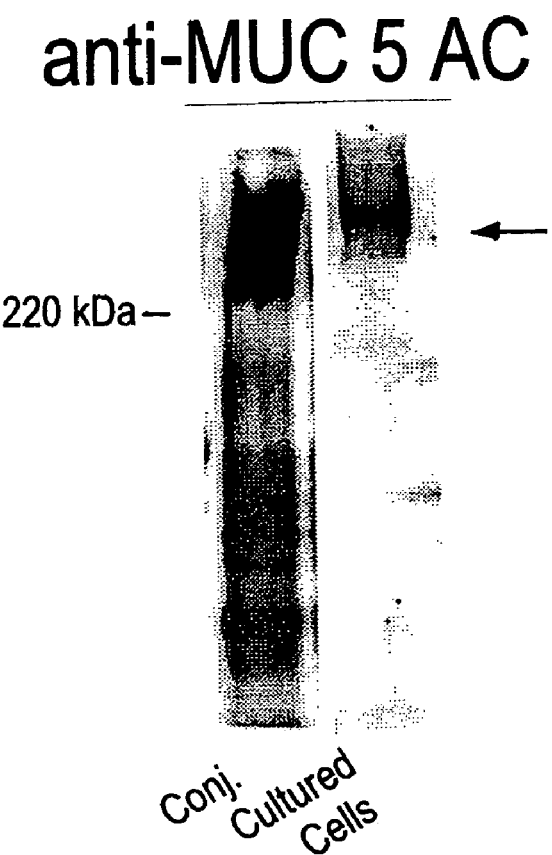
Figure 12:
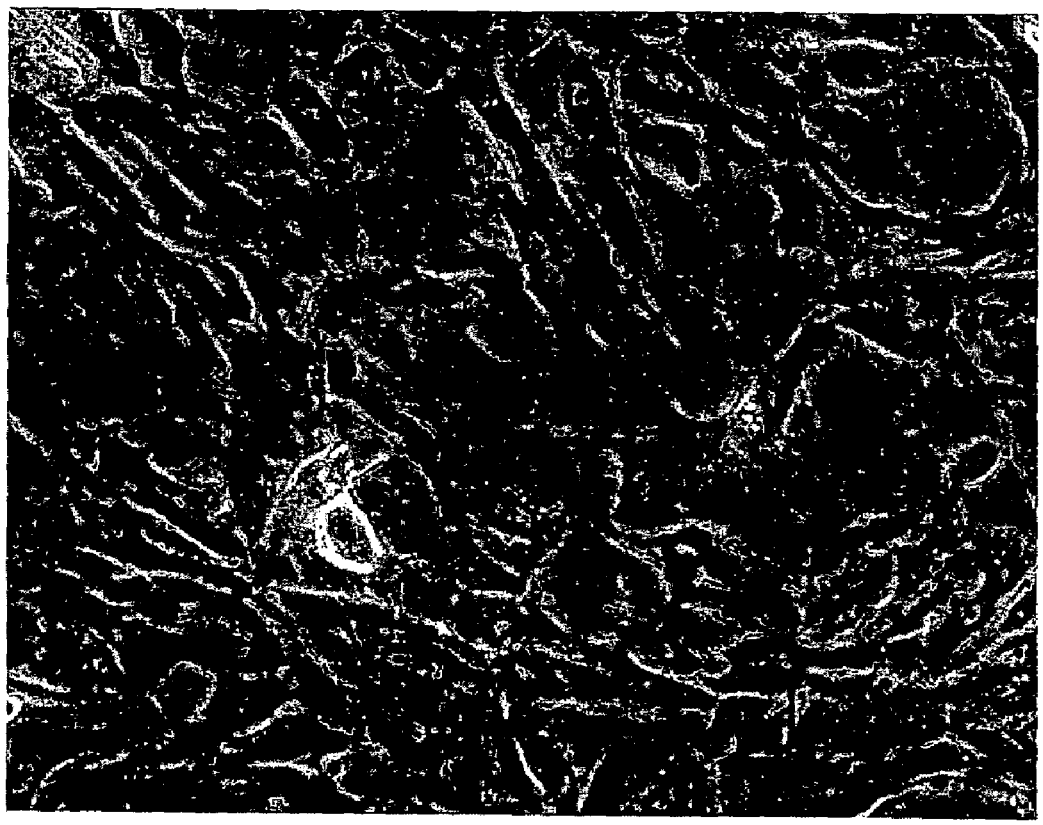
Figure 13:
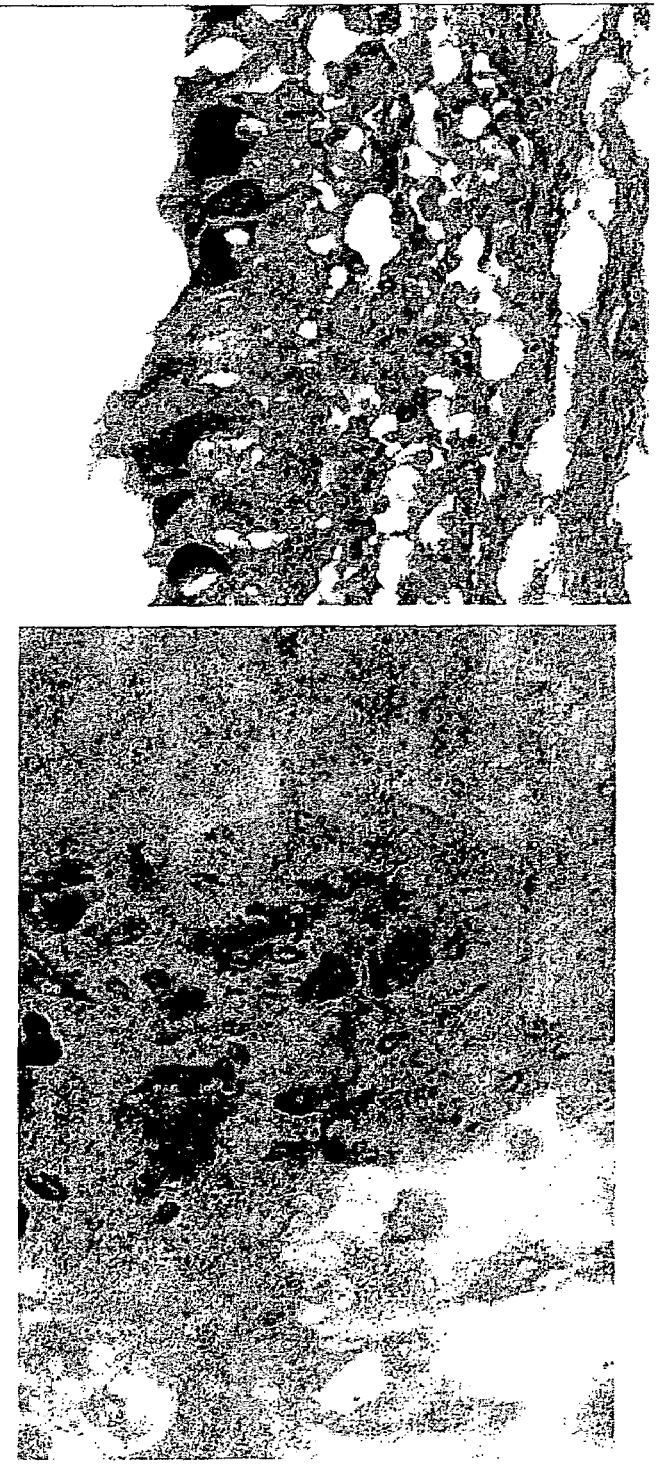
Figure 14:
Figure 15:
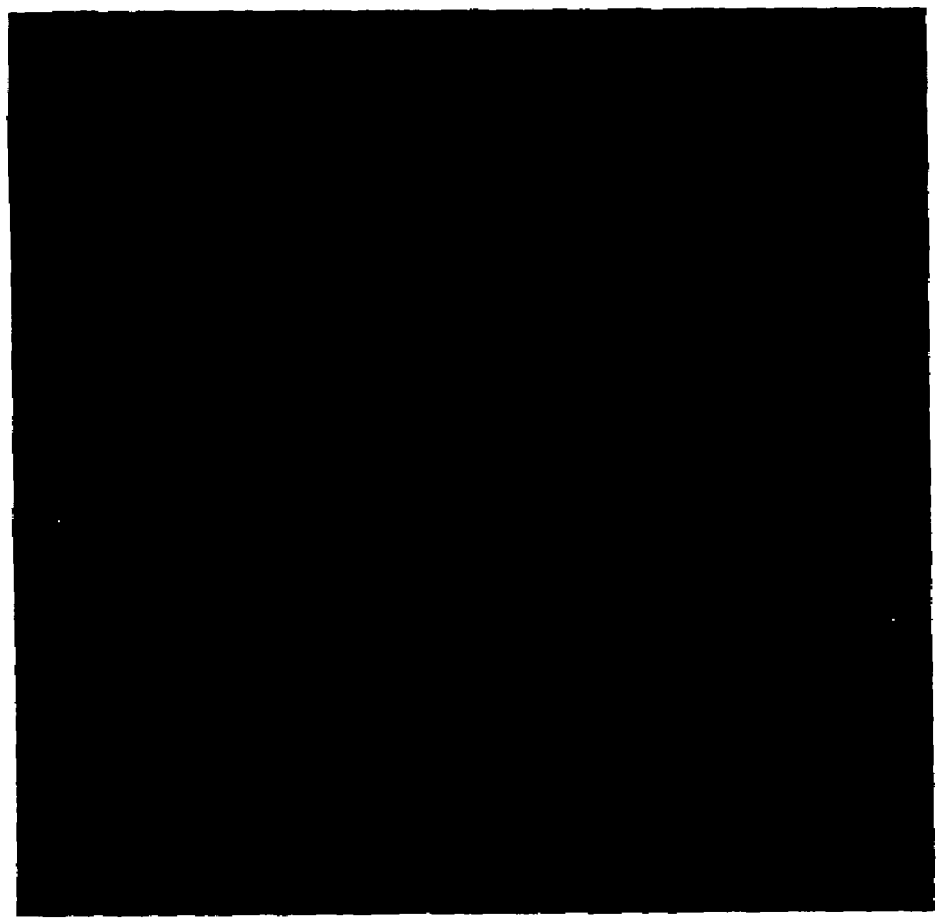
Figure 16A:
Figure 16B:
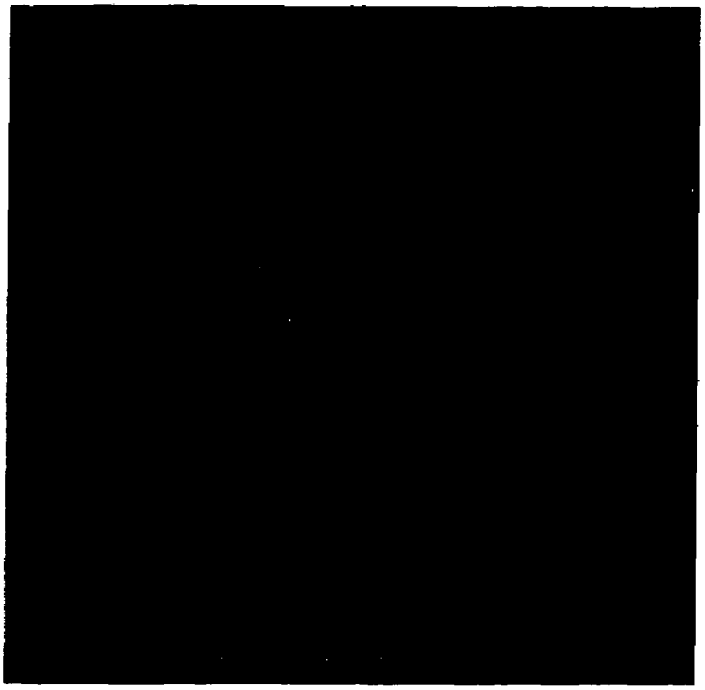
Figure 17B:
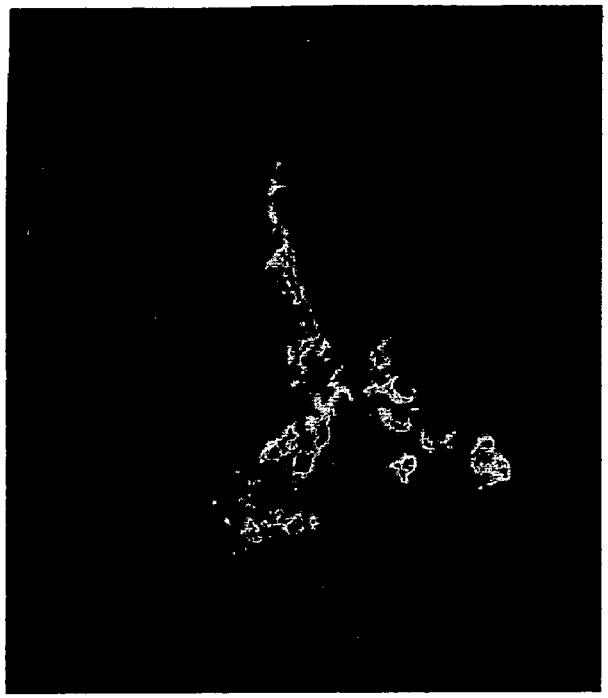
Figure 17A:
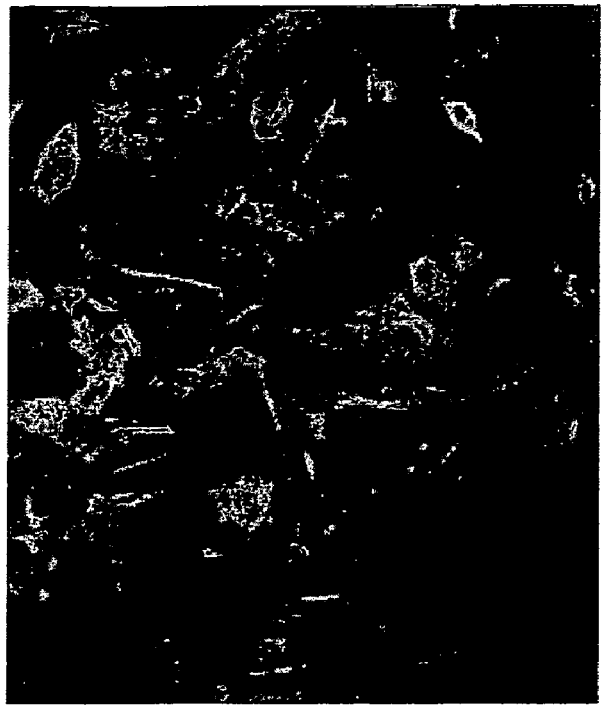
Figure 19:
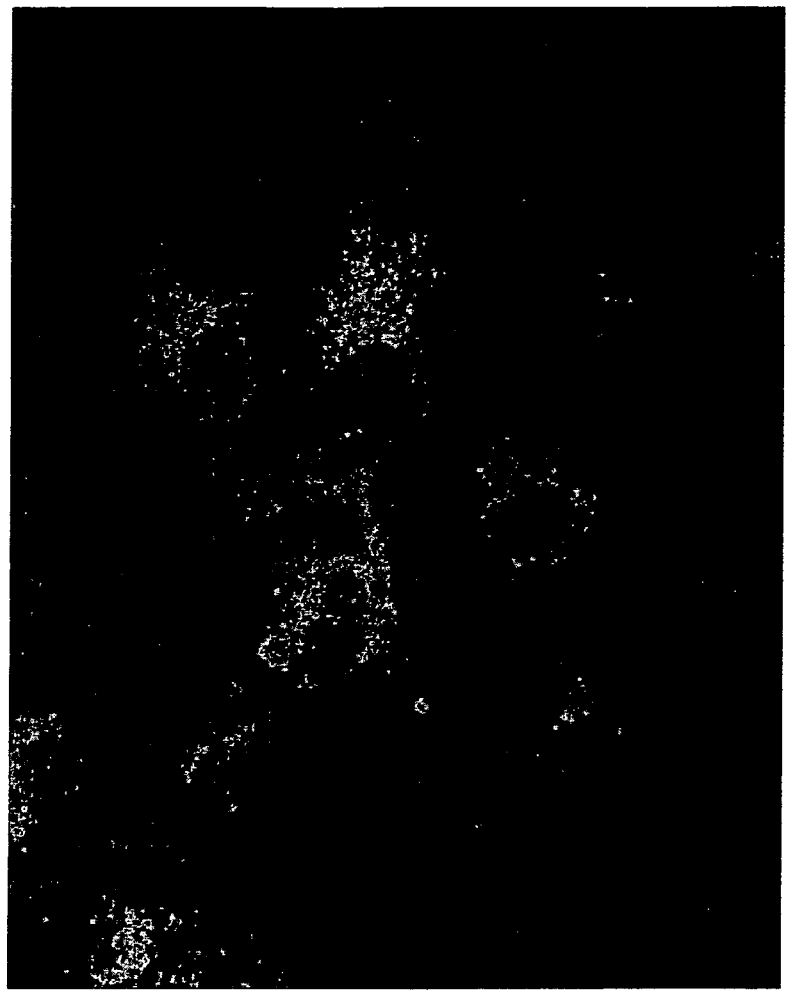

(CK-7), a specific marker of intermediate filaments associated exclusively with goblet cells (Magnification 200×);

FIGS. 8A and 8B depict an immunocytochemical localization of cytokeratin-4 (a negative control). Primary cultures of goblet cells isolated by a modified explant culture technique were mostly negative for cytokeratin-4. An occasional stratified epithelial cell is infrequently present on top of the underlying goblet cells (FIG. 8A). The underlying goblet cells are shown in (FIG. 8B) (Magnification 100×);

FIGS. 9A and 9B depict an immunocytochemical reactivity of goblet cells to the muscarinic receptor subtype 3 ($M_3$) shown in a primary, mixed conjunctival explant culture (FIG. 9A) and in rat conjunctival tissue (FIG. 9B). Only goblet cells stain for the $M_3$ receptor (Magnification 100×);

FIGS. 10A and 10B depict the transmission electron micrographs of two representative cultured goblet cells sectioned en-face. These cells display degrees of cell polarity and the presence of numerous, intact secretory granules (Magnification 6000×);

FIGS. 11A and 11B depict the Western blot analysis of UEA-1 containing high molecular weight glycoprotein (FIG. 11A) and MUC5AC in cultured goblet cells and homogenized conjunctival epithelium (FIG. 11B);

FIG. 12 depicts a phase contrast micrograph showing a representative primary culture of human goblet cells (Magnification 200×);

FIGS. 13A and 13B depict histochemical reactivity of cultured human goblet cells positive for AB-PAS. Cultured cells stained with AB/PAS displayed both acidic (blue) and neutral (pink) glycoconjugates associated with the cells. In addition, as a positive control, goblet cells within conjunctival tissue reacted positively to AB/PAS (Magnification 200×);

FIG. 14 depict an immunocytochemical staining for cytokeratin 4 in a culture of human goblet cells. Cytokeratin 4 is a specific marker of stratified squamous epithelial cells, which the staining indicates that relatively few of these contaminating cell types are present in human goblet cell cultures (Magnification 200×);

FIG. 15 depicts an Immunocytochemical staining of cultured human goblet cells that are positive for cytokeratin 7, which is a specific marker of intermediate filaments associated specifically with goblet cells (Magnification 200×);

FIGS. 16A and 16B depict a positive histochemical reactivity to the lectin Helix pomatia agglutinin (HPA) in cultured human goblet cells and in goblet cells within human conjuctival tissue. HPA recognizes 1-galactosamine within the secretory granules of goblet cells (Magnification 200×);

FIGS. 17A and 17B depict an immunocytochemical staining of cultured human goblet cells that are positive for HPA and cytokeratin 7. This shows dual localization of HPA and cytokeratin 7 in both cultured goblet cells and goblet cells located in human conjunctival tissue. Cytokeratin 7 is identified by fluorescein labelling (green) and HPA by rhodamine labelling (red) (Magnification 200×);

FIGS. 18A and 18B depict an immunocytochemical localization of the goblet specific mucin MUC5AC. The cultured goblet cells are positive for MUC5AC, including goblet cells of human conjunctiva (Magnification 200×); and FIG. 19 depicts a positive immunocytochemical staining for MUC5AC in cultured goblet cells. MUC5AC is contained within the secretory granules of human goblet cells as shown (Magnification 500×).

DETAILED DESCRIPTION OF THE INVENTION

A "culture of goblet cells" designates a culture of goblet cells having at least a concentration of 10% or more of goblet cells. In a further embodiment, the concentration of goblet cells maintained in culture is preferably 10%-30%; more preferably 30%-50%, yet more preferably 50%-70%, still more preferably 70%-90%, most preferably 90%-95%, and still most preferably 95%-100%.

A "primary culture" or "non-immortalized culture" designates a culture of goblet cells, which can be cultured for a limited time without losing their original differentiation characteristics.

An "immortalized cell" designates cells which have been genetically engineered, allowing them to multiply indefinitely.

A culture with an "extended lifespan" has the capability of successive culturing, preferably at more than three passages, while retaining original differentiation markers of cells.

A "passage" designates the process consisting of taking an aliquot of a confluent or saturation culture of cells, inoculating a fresh medium with an aliquot of cells, and culturing the cells until confluence or saturation is obtained. The cells are thus traditionally cultured by successive passages in fresh media. Unlike the present invention, after successive passages of culture, cells ordinarily tend to lose their original differentiation characteristics. Human diploid cells, in particular, have a limited proliferative lifespan in culture. The present invention comprises a method of successive passaging of cultured goblet cells, which retains the cells original phenotypic characteristics in vivo. The culture of the present invention may be passaged at least three times or more.

An "original phenotypic characteristics" of goblet cells designate the presence of particular markers representative of goblet cells in vivo: e.g., positive staining for alcian blue/Periodic acid Schiff's (AB/PAS) reagent, cytokeratin 7, the lectins Ulex europaeus agglutinin-I (UEA-I) and helix pomatia agglutinin (HPA), MUC5AC and $M_3$ muscarinic receptor; negative staining for cytokeratin 4, $M_1$ muscarinic receptor and banderia simplicifolia lectin.

The invention relates to a method by which one can simply and reproducibly isolate and subculture conjunctival goblet cells, which exhibit morphological, histochemical, immunocytochemical, and biochemical markers indicative of goblet cells in vivo and retain these markers upon subcultivation. The culture of goblet cells in accordance with the present invention provides a more effective in vitro test format while retaining the original phenotypic characteristics associated with goblet cells in vivo. Suitable sources of goblet cells for culture by the present method include conjunctival tissues from mammals such as, but not limited to, humans, rats, mice, rabbits, cats, dogs, sheep, goats, cows, and pigs. In a preferred embodiment of the present invention, the conjunctival tissue may comprise the fornical region and the nictitating membrane.

Evidence is presented herein that primary cultures of goblet cells can be isolated from fragments of mammalian conjunctiva using a modified explant culture system. Primary and passaged cultures of mammalian goblet cells obtained from the fornical region of the conjunctiva and from the nictating membrane, reacted positively with Alcian blue/Periodic acid Schiff's reagent (AB/PAS) and with the goblet cell specific lectins, Ulex europaeus agglutinin-1 (UEA-1) and Helix pomatia agglutinin (HPA), similarly to their counterparts in vivo. They presented positive, selective staining for the intermediate filament, Cytokeratin-7 and for the mucin, MUC5AC, selective markers for goblet cells in vivo, and secreted mucin into their culture medium. Moreover, these same markers persisted after subcultivation.

Isolation, in vitro culture, and characterization of goblet cells were performed using the following materials and methods. The method of the invention is described with reference to the following, non-limiting exemplary protocol using both human and rat goblet cells. At the same time, those of ordinary skill in the art of cell culture will appreciate that certain minor substitutions can be made (e.g., changes to the culture medium), so as to adapt the present goblet cell culture system for use with various mammalian tissues.

Exemplary Materials and Methods

Materials

RPMI-1640 culture medium, L-glutamine, penicillin/streptomycin, Hank's Balanced Salt Solution, trypsin-EDTA solution were obtained from BioWhittaker (Walkerville, Ill.), fetal bovine serum from Hyclone Laboratories (Logan, Utah). Falcon tissue culture flasks, pipettes, and other routine plastics were obtained from Becton Dickson Labware (Franklin Lakes, N.J.). Glass coverslips were from VWR Scientific (San Francisco, Calif.). Lab Tek chamber slides were obtained from NUNC, Inc. (Naperville, Ill.). Monoclonal antibody against Cytokeratin 7 (CK7) was from ICN (San Francisco, Calif.) and against Ki-67 was from Novocastra Labotatories, Ltd (New Castle Upon Yyne, UK). Ulex europeus agglutinin lectin, (UEA-1) and Helix pomatia agglutinin lectin (HPA) directly conjugated with fluorescein isothiocyanate (FITC) or Texas Red were obtained from Pierce, (Rockford, Ill.). Banderia simplicifolia lectin (BS-1) conjugated to FITC was obtained from Vector Laboratories (Burlingame, Calif.). Polyclonal antibodies against $M_1$ and $M_3$ acetylcholine receptor (AchR) subtypes were obtained from Research and Diagnostics Laboratory (Berkeley, Calif.). All other chemicals unless otherwise specified were obtained from Sigma (St. Louis, Mo.). The cytokeratin 4 antibody was a gift of Dr. James Zieske, Schepens Eye Research Institute, (Boston, Mass.). Dr. Ilene Gipson, Schepens Eye Research Institute, (Boston, Mass.) provided antibodies to rat and human MUC5AC. Dr. Marsha Jumblatt, University of Louisville School of Medicine, (Louisville, Ky.) provided the antibody to human MUC5AC.

The following examples are presented to illustrate the advantages of the present invention and to assist one of ordinary skill in making and using the same. These examples are not intended in any way otherwise to limit the scope of the disclosure.

Methods

Isolation and culture of cells. All removal of tissue and subsequent manipulations of animals used in this study conformed to the guidelines established by the ARVO Statement for the Use of Animals in Ophthalmic and Vision Research and were approved by the Schepens Eye Research Institute Animal Care and Use Committee. Male Sprague-Dawley rats weighing between 250 and 300 g were used in this study and were obtained from Taconic Farms (Germantown, N.Y.). Rats were anesthetized for 1 minute in $CO_2$, decapitated and both eyes surgically removed. Conjunctival tissue, more specifically the nictating membranes and/or fornix, were excised and immediately placed into Hank's Balanced Salt Solution containing 3× penicillin/streptomycin (300 µg/ml). Tissue was finely minced into 1-2 $mm^3$ pieces that were anchored onto either scored culture dishes or onto glass coverslips placed within 6-well culture dishes. The culture dishes contained just enough medium to cover the bottom of the dish (e.g., 400-500 µl), so that the tissue would receive nutrients via surface tension. (Otherwise, if the tissue was submerged, it became necrotic.) Cell medium used to feed explants and culture goblet cells consisted exclusively of RPMI -1640 medium supplemented with 10% heat-inactivated fetal bovine serum (FBS), 2 mM L-glutamine and 100 µg/ml penicillin-streptomycin. Explants were refed every two days with the medium described above and were grown under routine culture conditions of 95% $O_2$:5% $CO_2$ at 37° C.

Figure 1:
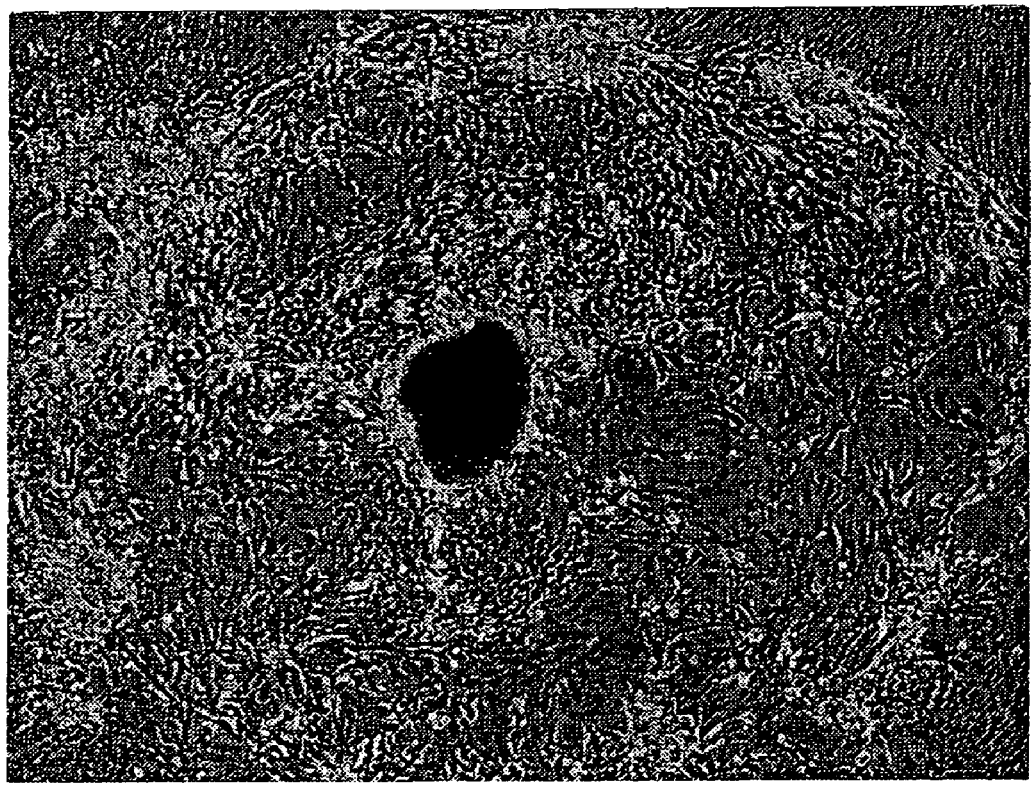
FIG. 1 is a phase contrast photomicrograph showing a representative explant culture of rat conjunctival tissue grown in RPMI-1640 culture medium supplemented with 10% FBS. Cells are seen growing out of the tissue plug within days of establishment of the culture. After 7-20 days, the tissue plug and its cells are surrounded by a ring of nodules (Magnification 40×)

Cells were permitted to grow from the explant plug until evenly spaced nodules were evident forming a circular pattern around the explant plug (see, e.g., FIG. 1). The explant plug was then removed and discarded, while leaving the nodules to grow goblet cells. At this juncture, all cells that grew outside this circular perimeter, or cells that grew separately from the nodules, were removed by scraping the bottom of the dish with a rubber policeman, and discarded. Goblet cells and cells of neural lineage then were observed to grow from these nodules, eventually covering the remainder of the culture vessel. Some cultures were trypsinized and passaged after reaching confluence. Cells were routinely passaged by trypsinization of confluent, adherent cells with 0.05% trypsin, 0.53 mM EDTA, pH 7.4.

Histochemistry. Cells were fixed with 100% methanol and processed for AB/PAS (Sheehan et al.) and lectin histochemistry. Goblet cells examined for lectin histochemistry were grown on either chamber slides, glass coverslips or plastic tissue culture wells, rinsed in PBS, and fixed in 100% methanol for 15 min at room temperature before they were returned to fresh PBS. Fixed cells were incubated in blocking buffer which consisted of 1% BSA and 0.2% Triton X-100 in PBS for 30 minutes at room temperature. Cells then were incubated for 1 h at room temperature with either UEA-1 conjugated directly to FITC diluted 1:100 in PBS, BS-1 conjugated to FITC diluted 1:200 or HPA conjugated to Texas Red and diluted 1:100 in PBS.

Immunocytochemistry. Methanol-fixed cells were examined for the presence of Cytokeratins 4 and 7 and MUC5AC. Slides with cultured goblet cells were incubated for 30 minutes at room temperature in blocking buffer that contained 1% BSA and 0.2% Triton-X in PBS. Cells were then incubated with the following dilutions of primary antibodies for 1 hour at room temperature. Antibody to Cytokeratin 7, which recognizes a goblet cell specific keratin, was diluted 1:15 in PBS. Antibody to Cytokeratin 4, specific for stratified, squamous, non-goblet epithelial cells, was diluted 1:10 in PBS. Antibody to rat MUC5AC, specific for mucin produced by goblet cells, was diluted 1:2000 and 1:4000 in PBS. Antibody to human MUC5AC was diluted 1:1000 in PBS. In order to investigate the proliferation profile of cultured goblet cells, antibody to human Ki-67 nuclear antigen was diluted 1:100 in PBS. For muscarinic receptor subtypes $M_1$ and $M_3$, methanol-fixed cells were incubated in blocking buffer that contained 1.5% normal goat serum and 0.2% Triton X-100 in PBS for 30 minutes at room temperature. Their respective antibodies were each diluted 1:2000 in PBS and incubated overnight at 4° C. The secondary antibodies, conjugated to either FITC or rhodamine were diluted 1:200 in PBS and incubated for 1 h at room temperature.

Slides, coverslips or dishes were washed 3 times in PBS after which coverslips were mounted with a media containing 100 mM Tris, pH 8.5, 25% glycerol, 10% polyvinyl alcohol, and 2.5% 1,4-diazobicyclo-[2.2.2]-octane. Cells were viewed using a Nikon Eclipse TE 300 inverted phase contrast microscope equipped for fluorescence while cells adherent to glass coverslips or microscope slides were visualized with a Nikon Eclipse E 800 fluorescence microscope. Negative controls consisted of substituting PBS for the primary antibody. Additional positive controls included frozen and/or fixed sections of rat conjunctiva containing prominent goblet cells.

Transmission Electron Microscopy. Cell-conditioned medium was removed from confluent cultures of goblet cells after which monolayers were washed with cacodylate buffer pH 7.3. Cells were fixed with cacodylate buffered Karnovsky's solution, post-fixed in 1% osmium tetroxide and embedded in epon according to standard transmission electron microscopy techniques. Thin sections, mounted on copper grids, were stained with lead citrate and examined with a Philips 410 transmission electron microscope (Philips, Eindhoven, The Netherlands).

Measurement of goblet cell mucin secretion. Cell-conditioned medium was collected at various time points following culture (48 hrs, 72 hrs) in order to measure the amount of mucin released by goblet cells. The amount of high molecular weight glycoconjugate, an index of mucin secretion, was determined by ELLA using a biotinylated lectin, UEA-1, known to react with specific carbohydrates present in terminal sugars on mucins synthesized, stored and secreted by goblet cells [21]. The ELLA was performed following the manufactor's protocol (Pierce, Rockford, Ill.). Biotinylated UEA-1 was used at 2 μg/ml, strepavidin conjugated to alkaline phosphatase was used at 1 μg/ml and the substrate p-nitrophenyl phosphate used at 2.5 mM. A 250 μl aliquot of the cell-conditioned medium was placed on a MaxiSorb titer microplate (Nalge, NUNC, Inc. Naperville, Ill.), and dried overnight at 40° C. Non-specific binding sites were blocked with 3% BSA, 0.05% Tween-20, and 0.15 M NaCl in 0.25 mM Tris-HCl (pH 7.5). Wash buffer contained 0.3% BSA, 0.05% Tween-20 and 0.15 M Nacl in 0.25 mM Tris-HCl (pH 7.5). The amount of UEA-1 detectable glycoconjugates in the goblet cell conditioned media were determined in duplicate using a microplate reader model MR 700 (Dynatech Labs, West Sussex, UK). A standard curve was constructed using bovine submaxillary gland mucin.

Electrophoresis and immunoblotting. Forty-eight hour old cell-conditioned medium was removed from young, middle-aged, old and pooled cultures of goblet cells and stored at 4° C. The remaining cells were scraped and collected into homogenization buffer containing 30 mM Tris-HCl, pH 7.5, 10 mM EGTA, 5 mM EDTA, 1 mM DTT, 10 mg/ml PMSF and 5 units/ml aprotinin. Cells were further lysed by sonication and whenever necessary, by freeze-thawing of the cell pellet. To determine the presence of MUC5AC, a goblet cell-specific mucin, and the glycoconjugate recognized by UEA-1, proteins present in goblet cell-conditioned medium and cell lysates were separated by SDS-PAGE using 6% gels and transferred to nitrocellulose membranes as described by Towbin et al. To measure UEA-1 detectable glycoconjugates, the membranes were blocked overnight at 4° C. in 5% dried milk in TBST consisting of 10 mM Tris-HCl, pH 8.0, 500 mM NaCl, and 0.05% Tween-20 and then incubated with biotinylated UEA-1 (1:100) for 1 h at room temperature. The nitrocellulose membranes were washed three times with TBST and then incubated with a 1:2500 dilution of horseradish peroxidase-labeled strepavidin in TBST for 1 h. The membranes were washed three times after which the UEA-1 reactive glycoconjugates were visualized using the enhanced chemiluminescence method. Homogenized adult rat conjunctival tissue was used as a positive control. In order to detect MUC5AC, membranes were blocked for 1 h as described above and incubated with anti-human MUC5AC antibody (1:500) in 5% dried milk overnight at 4° C. (Jumblatt et al.). The membranes were washed, then incubated for 1 h at room temperature with a secondary antibody conjugated to horseradish peroxidase in 5% dry milk. They were washed and developed using the enhanced chemiluminescence method as before.

ELISA analysis of human cultured goblet cells using MUC5AC antibody. Materials that were used include the following: Primary antibody MUC5AC (NeoMarker Cat#45 ml) solution adjusted to an appropriate concentration (approximately 2 μg/ml) with wash buffer; anti-mouse IgG-HRP, which was adjusted to a concentration of approximately 1 μg/ml with wash buffer; bovine submaxillary Mucin type I (Sigma) standard solution at 10-200 μg/ml in coating buffer; a coating buffer consisting of 0.1M sodium bicarbonate buffer at pH 9.2; TBST at 25 mMTris, 150 mM NaCl, pH7.5, 0.05% Tween® 20; blocking buffer consisting of TBST and 3% crystalline BSA (Sigma); wash buffer consisting of TBST, 0.3% crystalline BSA (Sigma); substrate solution of dissolved tablet of O-phenylenediamine Dihydrochoride (OPD) in 0.2 M dibasic sodium phosphate, and 0.1 M citric acid solution followed by the addition of 4 μl of 30% $H_2O_2$ in a final volume of 10 ml; and titer microplate MaxiSorb, Nalge NUNC.

The method of ELISA analysis included adding 100 μl of mucin standard solution, 100 μl of cells lysated, or 250 μl aliquot of the culture medium on a titer microplate (MaxiSorb; Nalge NUNC) and dried overnight at 40° C. Each well were rinsed with 3×200 μl of wash buffer. 200 μl of blocking buffer were added to the well and incubate for 30 minutes at 37° C. Each well were rinsed with 3×200 μl of wash buffer. 100 μl of primary antibody MUC 5AC solution were added and incubated for 1 hour at 37° C. Each well was rinsed with 3×200 μl of wash buffer. 100 μl of anti-mouse IgG-HRP were added and incubated for 1 hour at 37° C. Each well were rinsed with 3×200 μl of wash buffer. 100 μl of the substrate were added to each well and performed colorimetric reaction.

EXAMPLE I

Growth and Morphology of Goblet Cells in Culture

Figure 2A:
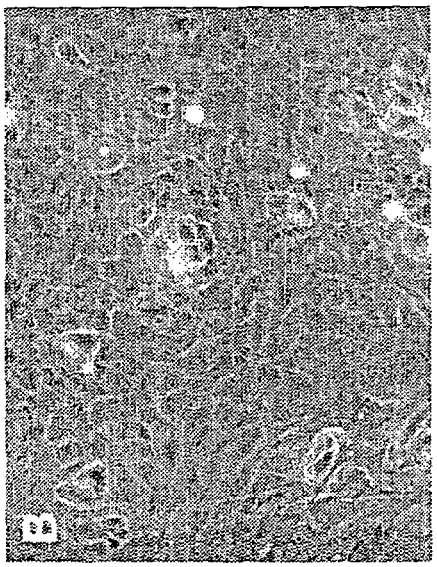
FIGS. 2A, 2B, 2C, and 2D show photomicrographs illustrating the growth patterns of conjunctival explants in vitro. When examined closely, each nodule (arrow) is the apparent source of numerous goblet cells, which traverse the underlying epithelial cells (FIG. 2A). The single cells move along the epithelium until they find an empty space and adhere to the bottom of the culture flask exhibiting a cobblestone morphology (FIG. 2B). Goblet cells contain tiny translucent droplets, which are similar in appearance to mucin on their surface (FIG. 2C). As goblet cells grow in vitro, so do the droplets. They often appear as if the mucin droplets are released off and secreted into the cell medium (FIG. 2D) (Magnification 100×)
Figure 2B:
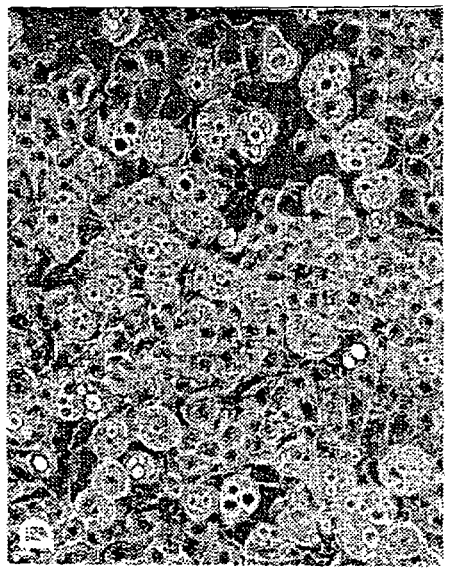
Figure 2C:
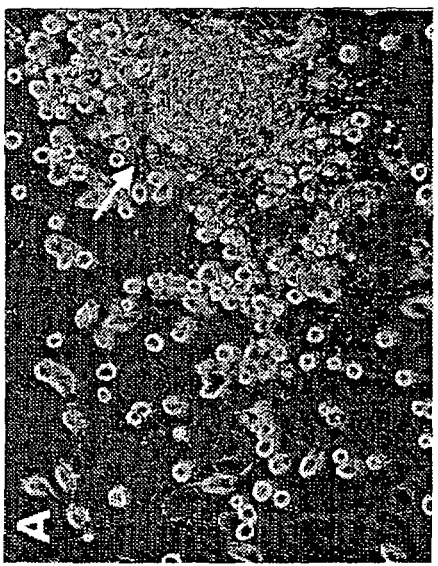
Figure 2D:
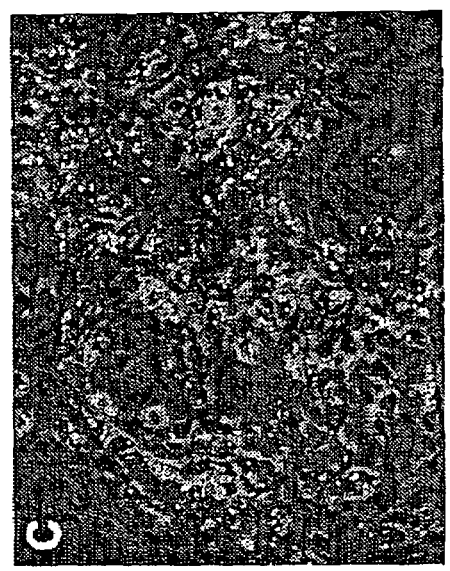

As early as 24 hours after establishment of the organ culture, adherent cells were visible around most sides of the tissue plug. By 36-48 hours, cells displaying a cobblestone morphology were observed. Within 7-10 days of culture, evenly spaced nodules were observed, which formed a circular pattern around the plug of conjunctival tissue (FIG. 1). Initial attempts at locating goblet cells within this mixed population of cells utilized AB/PAS (a well-documented stain for glycoconjugates in fixed tissue sections). The nodules depicted in FIG. 1 reacted strongly to AB/PAS displaying a dark blue stain indicative of acidic mucin. To further purify potential goblet cells, one nodule was grown in the culture dish. All other cells were scraped from the surface of the vessel using a rubber policeman and the nodule was thoroughly rinsed to rid the culture of floating, non-goblet cells. The nodule was refed with RPMI-1640 medium supplemented with 10% FBS. Within several days, goblet cells were seen leaving the nodule (FIG. 2A). Initially they assumed a rounded morphology but within 7-10 days they migrated away from the parent nodule and formed circular clusters of cells, which often presented a semicuboidal morphology (FIG. 2B). The classical chalice-like appearance of the goblet cell was not observed in cultured cells. Often, as cells proliferated in culture, tiny droplets were visible on the surface of cultured goblet cells suggestive of a secretory product (FIG. 2C). As these droplet-containing cells grew in culture, the droplets increased in size and number (FIG. 2D). Finally, one could see strands of fibrous material strewn over the cells (data not shown). Upon reaching confluence, cultures were trypsinized and passaged. The goblet cell cultures described here have been passaged three to five times without losing morphological integrity.

These studies demonstrated that rat conjunctival goblet cells can be isolated from the fornix and the nictating membrane using a modified explant culture system. Moreover, the cells can be grown and propagated in uncoated tissue culture vessels and nourished in a basic culture medium supplemented only with fetal bovine serum, 1-glutamine and antibiotics. Currently, RPMI medium is considered to be a non-conventional medium in the goblet cell literature. By happenstance, RPMI medium was found to be more effective than the usual types of mediums used in other studies that failed to successfully grow isolated goblet cells. Cultures derived in this manner can be kept relatively (>90%) pure by scraping contaminating cell types from the culture dish. These cultured cells proliferate in vitro and can be passaged at least three times, with full retention of identifying cellular markers and functional activity.

EXAMPLE II

Proliferation of Goblet Cells in Vitro

Figure 3:
FIG. 3 is an immunocytochemical reaction of the nuclear antigen Ki-67 with cultured goblet cells. Goblet cells in primary and passaged culture react positively with Ki-67 which selectively stains the nuclei of cells actively engaged in proliferation as shown here (Magnification 250×)

The proliferation profile of the goblet cell cultures was assessed by staining the cells with an antibody against Ki-67 antigen, a nuclear and nucleolar protein which is exclusively expressed in proliferating cells. (Gerdes et al., 1983; Gerdes et al., 1984) All cultures were routinely evaluated for Ki-67 reactivity. Ki-67 is localized in all primary and passaged cultures of conjunctival goblet cells indicating that our cells are actively proliferating in vitro. As shown in FIG. 3, greater than 30% of the goblet cells in this primary culture were actively proliferating as indicated by their reactivity to Ki-67. During the course of these studies, it was observed that the number of Ki-67 positive cells correlated with the degree of confluence of any given culture. As the cells approached confluence, the number of proliferating cells declined both in primary and passaged cultures.

EXAMPLE III

Characterization of Cultured Goblet Cells

Figure 4A:
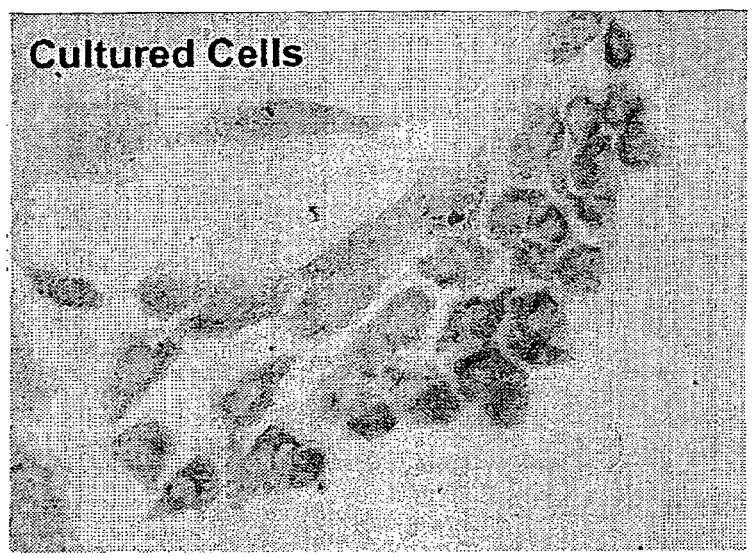
FIGS. 4A, 4B, and 4C depict histochemical reactivity of cultured goblet cells to AB-PAS. Goblet cells stain intensely with AB/PAS indicating the presence of both acidic (blue) and neutral (pink) glycoconjugates associated with the cells (FIG. 4A) (Magnification 100×). Goblet cells which appeared to contain secretory droplets on their surface also reacted strongly to AB/PAS staining a pinkish color while the droplets themselves stained bright red indicating the presence of with a neutral mucin product (FIG. 4B) (Magnification 600×). As a positive control, secretory products present in goblet cells of the conjunctiva reacted positively to AB/PAS (epi, epithelium) (Magnification 200×)
Figure 4B:
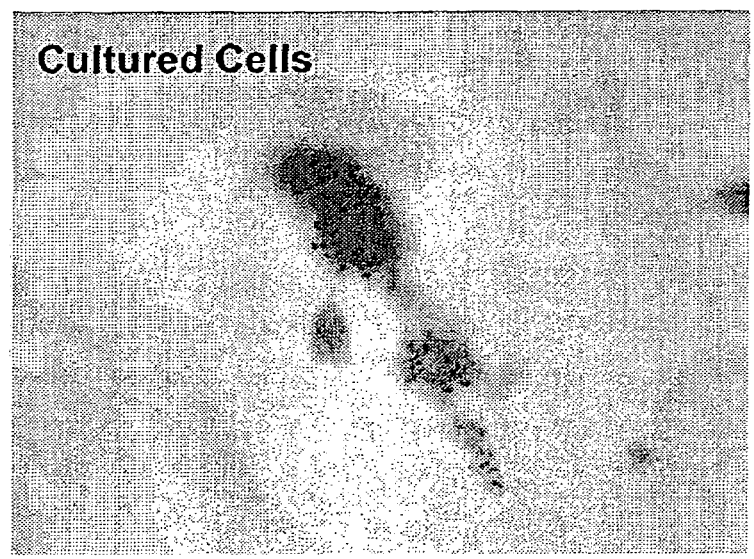
Figure 4C:

Although AB/PAS was used as a screening mechanism to aid in the identification and subsequent purification of the goblet cell cultures, it was important to determine whether or not these purified cells retained positive reactivity to AB/PAS. The present results show that both primary and passaged cultures react histochemically with the stain. Shown in FIGS. 4A (rat) and 13A (human) are cells grown from a representative primary culture in which the cell nuclei are stained blue and displayed a red vesicle-filled cytoplasm. Further staining examined the reactivity of goblet cells, which appeared to contain secretory droplets on their surface. These cells (FIG. 4B) stained a reddish color with no visible demarcation of the nucleus. Droplets located on top of the cells were bright red, indicating that these cells were associated with a basic type of mucin secretion product. Often, cultures appear covered with what appeared to be a fibrous material. Upon examination, both the cells and their accompanying fibers reacted positively to AB/PAS, staining a dark blue to purple color indicative of an acidic mucin product. The reactivity of the present goblet cell cultures to AB/PAS was not lost upon subcultivation, contrary to other reports (Adams et al., 1989). AB/PAS reactivity of goblet cells in culture was compared with that of goblet cells in vivo (FIGS. 4C (rat) and 13B (human)).

Figure 5A:
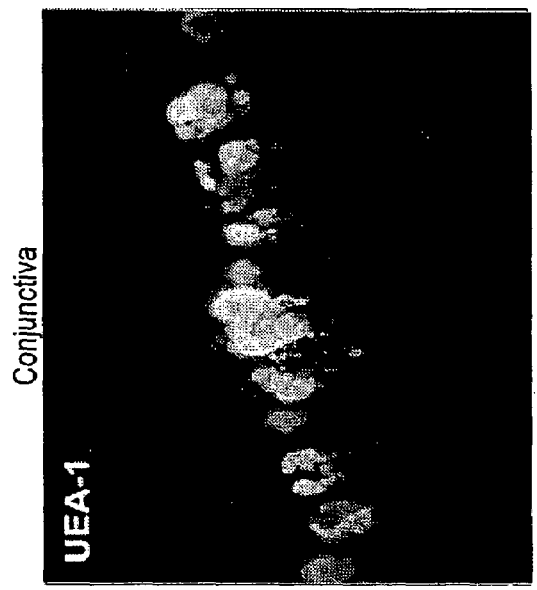
FIGS. 5A, 5B, 5C, and 5D depict Lectin histochemistry confirming that rat conjunctival goblet cells were associated with UEA-1, which recognizes the 1-fucose moiety of glycoproteins in the secretory granules of goblet cells (FIG. 5A) and the secretory product in goblet cells located in the conjuntiva (FIG. 5B). In addition, both primary culture goblet cells (FIG. 5C) and goblet cells present in sections of rat conjunctiva (FIG. 5D) were reactive to HPA, which recognizes 1-galactosamine within their secretory granules (epi, epithelium) (Magnification 200×)
Figure 5B:
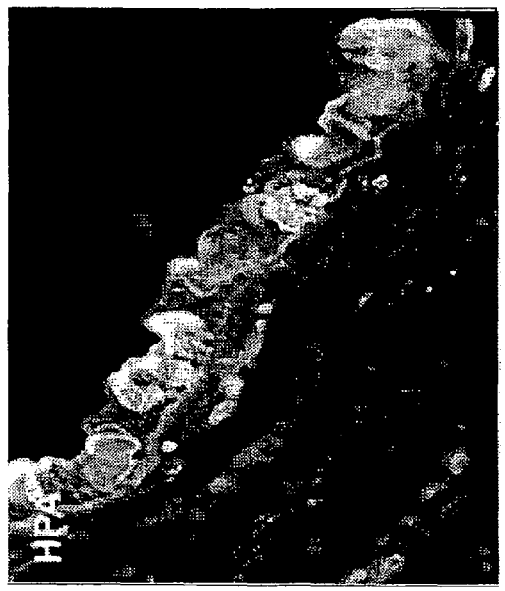
Figure 5C:
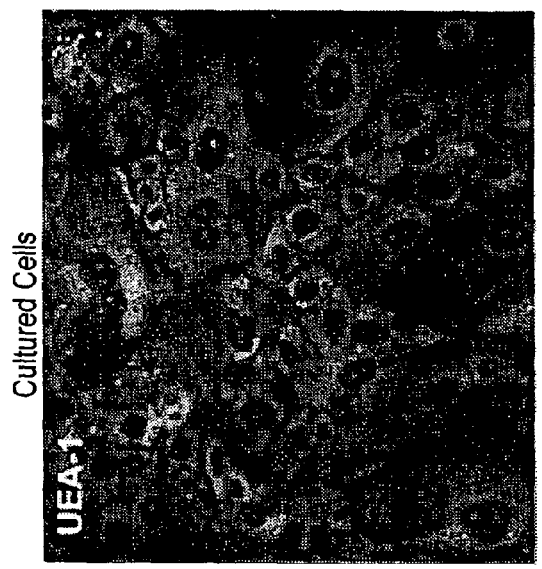
Figure 5D:
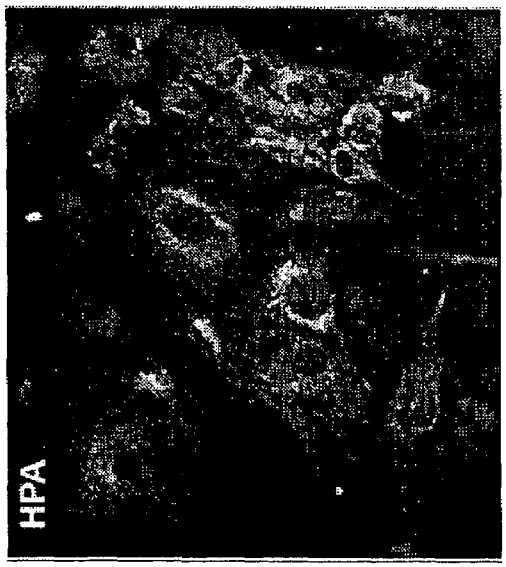

Additional histochemical verification of these goblet cell cultures was accomplished using a panel of lectins as histochemical probes. UEA-1 recognizes the L-fucose moiety of glycoproteins in the secretory granules of conjunctival goblet cells while HPA recognizes L-galactosamine within the secretory granules of goblet cells. BS-1, used here as a negative control, recognizes the n-galactosyl groups of glycoproteins in stratified squamous epithelial cells. Both primary and passaged cultures of goblet cells were labeled with anti-UEA-1 and HPA (FIG. 5) antibodies directly conjugated to a fluorophore. Goblet cells in culture were found to react positively to UEA-1 as evidenced by cytoplasmic staining (FIG. 5A). The reactivity of cultured goblet cells to UEA-1 was similar to that of goblet cells located in conjunctival tissue (FIG. 5B). Similar results were observed with HPA (FIGS. 5C, 5D (rat) and 16A, 16B (human)). Both goblet cells in culture and in conjunctival tissue were found to react positively to HPA. Passaged cells also reacted positively to both UEA-1 and HPA. The reaction to these lectins varied and appeared to be related to the levels of mucin associated with the cell at the time it was processed for lectin histochemistry. Goblet cells did not react with BS-1 (data not shown).

Figure 6A:
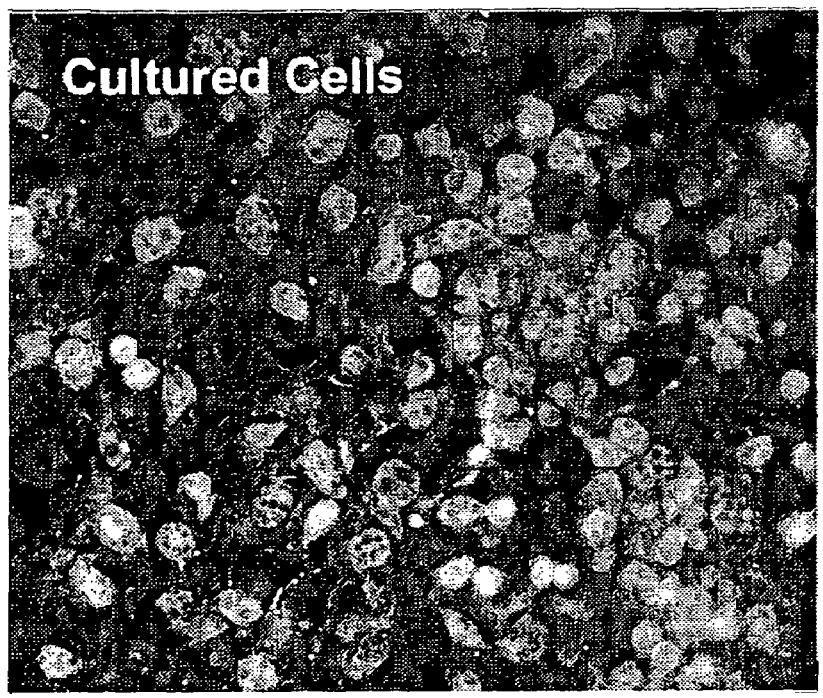
FIGS. 6A and 6B depict an immunocytochemical localization of MUC5AC indicating that secretory products of cultured goblet cells (FIG. 6A) and goblet cells located in conjunctival tissue (positive control) (FIG. 6B) contain mucin. Almost all cells were positive for MUC5AC when visualized using fluorescence microscopy (Magnification 100×)
Figure 6B:

Immunocytochemical localization of the following markers was undertaken to assist in the characterization of the cultured goblet cells and consisted of the following antibodies: MUC5AC, a mucin specifically produced by conjunctival goblet cells (Inatomi et al.); Cytokeratin-7 an intermediate filament associated solely with goblet cells (Krenzer et al.); Muscarinic $M_3$ recently identified as being associated with goblet cells in the adult rat conjunctiva (Rios et al.); Cytokeratin-4, specific to the intermediate filaments found in stratified squamous epithelial cells and Muscarinic $M_1$ receptor subtype associated with the stratified squamous epithelial cells but not goblet cells. Primary and passaged cultures of goblet cell cytoplasm stained intensely for MUC5AC while no staining was observed in the neighboring epithelial cells (FIG. 6). As a positive control, goblet cells within rat conjunctival tissue stained intensely for MUC5AC (FIG. 6B).

Figure 7A:
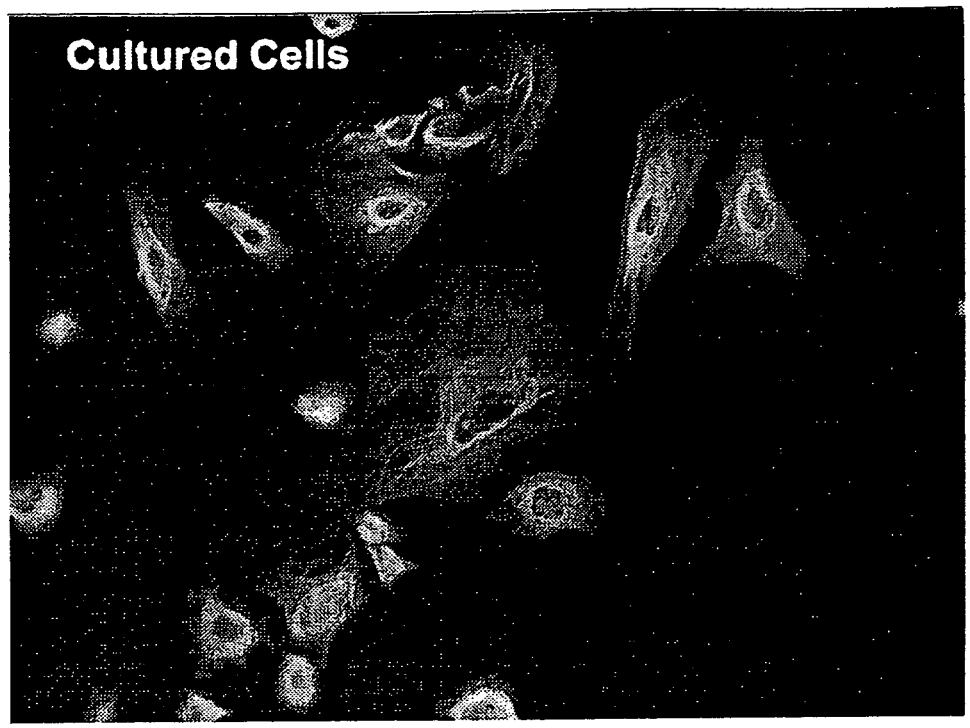
FIGS. 7A and 7B depict cultured goblet cells (FIG. 7A) and goblet cells in conjunctival sections (FIG. 7B) displaying intense immunocytochemical staining for cytokeratin-7
Figure 7B:
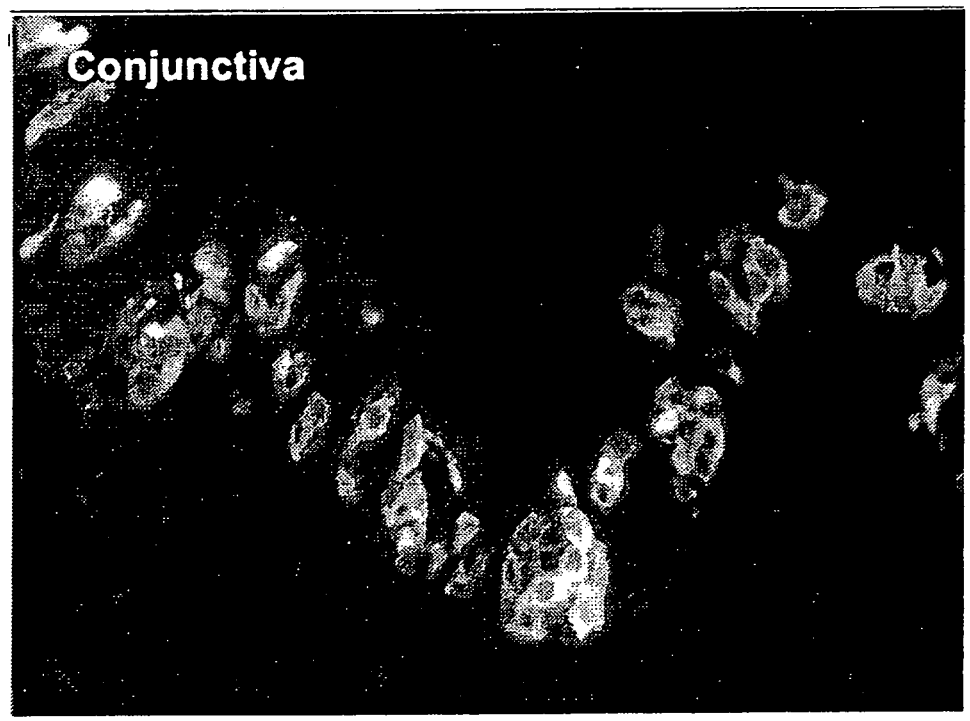

Goblet cells in mixed cultures (FIGS. 7A (rat) and 15 (human)) and in conjunctival tissue (FIG. 7B) displayed intense fluorescence for cytokeratin-7 whereas other epithelial cell types were negative for this intermediate filament. Conversely, when similar, mixed cultures were analyzed for cytokeratin-4, positive immunofluorescence was observed only in epithelial cells migrating over the underlying goblet cell clusters (FIGS. 8A, 8B, and 14). In addition, only the $M_3$ receptor subtype was positive both in cultured cells (FIG. 9A) and in goblet cells in conjunctival sections (FIG. 9B).

M3 muscarinic receptors were detected subjacent to the secretory granules of goblet cells in the conjunctiva (FIG. 9B). Several types of adjacent epithelia in conjunctival sections showed positive immunofluorescence for the M1 receptor, but cultured goblet cells did not (data not shown).

When the cultured goblet cells were studied using transmission electron microscopy (FIGS. 10A and 10B), typical goblet cell morphology was observed. En-face sections of goblet cells revealed cells, which contained many large storage granules, with the nucleus often asymetrically placed.

EXAMPLE IV

Mucin Secretion by Goblet Cells in Vitro

UEA-I was used to measure glycoconjugate secretion from primary and passaged goblet cells using an ELLA (Rios et al.). Goblet cells, which had been in serum-free medium for 48 hours and had covered 20 and 40% of the surface of a 35 $cm^2$ culture dish secreted a total of 49 and 160 µg of mucin respectively. Other cultures also incubated in serum-free medium for 72 hours which covered 10 and 256 of the same type of culture vessel were found to secrete a total of 50 and 64 micrograms of mucin, respectively. These data are shown in Table 1.

TABLE 1

UEA-1-containing glycoprotein secreted by rat goblet cells

| Sample # | Time in Culture (h) | % of plate covered by goblet cells | Total µg of mucin secreted |
|---|---|---|---|
| 1 | 48 | 20 | 48.9 |
| 2 | 48 | 35-40 | 159.9 |
| 3 | 72 | 10 | 49.9 |
| 4 | 72 | 25 | 63.5 |

EXAMPLE V

Western Blot Analysis for UEA-1 Detectable Glycoprotein and MUC5AC

Proteins from cell lysates of cultures of primary and passaged goblet cells were analyzed by western blot methods using biotinylated-UEA-1 and an antibody against MUC5AC. As shown in FIG. 11A, a high molecular weight glycoprotein of more than 220 Kda, indicative of UEA-1, was present in the lysate of cultured goblet cells. A similar band was also present in samples of rat conjunctival homogenate, the positive control used. Similarly, the human MUC5AC antibody reacted with a high molecular weight glycoprotein of more than 220 KDa indicating the presence of MUC5AC (FIG. 11B) in cultured goblet cell lysate. MUC5AC was also present in rat conjunctival homogenate.

EXAMPLE VI

Presence of MUC5AC Glycoprotein in Human Cultured Conjunctival Goblet Cells

Immunofluorescence analyses using a commercially available antibody against MUC5AC glycoprotein in human conjunctival sections revealed that MUC5AC is preferentially located in secretory granules of conjunctival goblet cells and not in conjunctival epithelium (FIGS. 18A, 18B, and 19).

To quantify the amount of mucin secreted by cultured human conjunctival goblet cells an ELISA analysis was perform by using commercially available antibody MUC5AC. As revealed by ELISA analysis, MUC5AC glycoprotein was detected in the culture media in excess of 200 µg/ml when compared with a standard.

EXAMPLE VII

Immortalizing Mammalian Goblet Cells

Mammalian goblet cells in accordance with the invention can be immortalized using standard procedures known by those of ordinary skill in the art. By using the method of culturing goblet cells described in the invention, an immortalized mammalian, preferably human, goblet cell line can be reproducible, while retaining the original phenotypic characteristics or differentiation markers of goblet cells generally found in vivo.

An exemplary method of producing a human immortalized goblet cell line includes the following protocols. Conjunctiva tissue may be obtained from a human donor. The tissue is prepared for culturing using the methods described above. pL PCL telomerase (TERT) is transfected into retroviral vectors, e.g., NIH 3T3 cells which serve as the packaging cell line, using standard procedures known in the art. Because human goblet cells have a limited proliferative lifespan in culture, telomerase, via a retroviral vector was inserted into the culture of human goblet cells. Telomerase is an enzyme that elongates olgionucleotides from the telomere, which extends the lifespan of the goblet cells without causing cellular tranformation and genomic instability. These retroviral particles can introduce TERT to the goblet cells but cannot replicate inside the goblet cells due to the fact that pL PCL hTERT does not contain the structural genes (gag, pol and env) which are needed for particle formation and replication. For instance, goblet cells are seeded into a growth medium, e.g., RPMI-1640, 12-18 hours before infection with TERT. For infection, medium is collected from growing packaging cells, filtered through a 0.45 micron cellulose acetate filter and applied to the goblet cells. 15 mls of packaging cell medium is applied to human goblet cells, which have been seeded in 100 mm tissue culture dishes. Following 12 hours of incubation with the packaging cell medium, polybrene is added to the culture medium to a final concentration of 8 micrograms per ml. Packaging cell medium is replaced after 24 hours of incubation with medium containing puromycin or an antibiotic, where only the telomerase infected cells survive. All noninfected cells are removed by aspiration of the cell medium. New medium is added to the transfected cells, which are allowed to grow and expand. The transfected cells are then tested for successful immortalization. The various studies can include, for example, testing telomerase activity, performing their karyotype, documenting the cellular lifespan and evaluating for histochemical (AB/PAS reactivity, HPA reactivity), for immunocytochemical (cytokeratin 7, MUC5AC), for biochemical (ability to secrete MUCSAC using ELISA protocol described above) and for molecular markers (PCR for MUC5AC) of human cultured goblet cells.

In summary, conjunctival tissue was surgically removed from Sprague-Dawley rats and human patients undergoing ocular surface surgery (Massachusetts Eye and Ear Infirmary, Boston, Mass.). (Other mammalian conjunctival tissue can also be used.) For the rats, goblet cells were then isolated from the nictating membrane and fornix using explant cultures. Human tissue were isolated from the superior fornix of the conjunctiva. Cells derived from the explants were grown and propagated in RPMI medium supplemented with 10% fetal bovine serum and characterized using an enzyme-linked lectin assay (ELLA) with the lectin Ulex europaeus agglutinin-1 (UEA-1), Western blot analysis, light and electron microscopy, specialized histochemistry and indirect immunofluorescence microscopy.

Goblet cells from mammalian conjunctiva were successfully isolated from conjunctival explants by scraping non-goblet cells from the culture vessel. Cultures have been passaged a minimum of three to five times without the loss of their specific cellular markers. The cultured cells fulfilled the following criteria, which enabled ready identification of them as conjunctival goblet cells: positive staining for AB/PAS reagent, cytokeratin 7, UEA-I and HPA, MUC5AC and $M_3$ muscarinic receptor; negative staining for cytokeratin 4, $M_1$ muscarinic receptor and banderia simplicifolia lectin. Measurements made by using the ELLA, revealed substantial amounts of UEA-I detectable high molecular weight glycoproteins and MUC5AC released into the medium.

Morphologically, although the cultured cells did not assume the typical in vivo goblet cell morphology, they contained numerous secretory vesicles, secreted droplets of mucin and as they matured in culture, strands of mucin were observed on top of the cultures. When analyzed by transmission electron microscopy, a well-described goblet cell morphology was observed where the cytoplasm was filled with many numerous, translucent, distinct secretory vesicles thus supporting the fact that they are not other types of epithelia. Histochemically, the cytoplasm of the cultured cells as well as their associated mucin droplets and strands reacted with AB/PAS and with the goblet cell-associated lectins UEA-I and HPA. The immunocytochemical markers cytokeratin-7, MUC5AC and muscarinic receptor, $M_3$ were expressed by the cultured cells. Moreover these cells were biochemically functional in vitro by retention of their ability to secrete mucin.

Proliferating goblet cells in culture, which fulfill morphological, histochemical, immunocytochemical and functional markers/functions of their in vivo counterparts, provide invaluable tools with which to delineate the pathobiology of the ocular surface and to study the many facets of goblet cell mucin synthesis and secretion in a direct, controlled and reproducible manner. Furthermore, the use of cultured goblet cells decreases dependence on the use and/or sacrifice of large numbers of animals to derive the same information. The availability of large numbers of cultured goblet cells will enable us to gain new information on the molecular, cellular, and functional levels, contributing to the development of novel therapies aimed at alleviating aberrant, mucin-induced diseases of the ocular surface.

USES

The cultured goblet cells of the invention do not only provide a good research tool, they are also useful for testing the toxicity, allergenicity, tumorigenicity, intolerance, and/or other harmful effect(s) of various compounds, such as those used in consumer products (e.g., contact lens, shampoo, other hair care products, soaps, etc.). Additionally, the goblet cell cultures may be used for pharmaceutical testing, such as testing the ability of different compounds to stimulate or to inhibit goblet cell secretion, proliferation and/or other function. The invention may also be used in treatment of diseases involving mucin deficiency (e.g., conditions related to or caused by dry eyes). For instance, goblet cells could be transplanted to the ocular surface of patients with decreased goblet cells and decreased mucin production using the methods of the present invention. The invention may also be used as a screening tool for, for example, to characterize determining laser surgery options. The present invention may be produced in a kit with instructions for experimenting the effects of mucin such as screening various products, diagnosing mucin deficiency, studying for allergic reactivity of various foreign substances and quantitating the amount of mucin. Autoimmune effects may be deterred by using patient's own goblet cells, from the good eye (for example), for culturing and autograft transplantation. Goblet cells, which may have been grown either on anmiotic or artificial membranes, may also be used for the development of corneal bandages for the repair of lacerated corneas or a mucin deficient condition.

REFERENCES

Adams A D. The morphology of human conjunctival mucus. *Arch Ophthalmol*. 1979; 97:730-734.

Adams G G, Dilly P N. Differential staining of ocular goblet cells. *Eye*. 1989; 3:840-844.

Allansmith M R, Baird R S, Greiner J V. Density of goblet cells in vernal conjunctivitis and contact lens-associated giant papillary conjunctivitis. *Arch Ophthalmol*. 1981; 99:884-885.

Breithnach R, Spitznas M. Ultrastructure of the paralimbal and juxtacaruncular human conjunctiva. *Graefe's Arch Clin Exp Ophthalmol*. 1998; 226:567-575.

Chao C W, Butala S M, Herp A. Studies on the isolation and composition of human ocular mucin. *Exp Eye Res*. 1988; 47:185-196.

Geggel H S, Gipson I K. Removal of viable sheets of conjunctival epithelium with dispase II. *Invest Ophthal Vis Sci*. 1985; 26:15-22.

Gerdes J, Schwab T, Gordon J. Production of a mouse monoclonal antibody reactive with a human nuclear antigen associated with cell proliferation. *Int J Cancer*. 1983; 31:13-20.

Gerdes J, Schwab U, Lemke H, Stein H. Cell cycle analysis of a cell proliferation-associated human nuclear antigen defined by the monoclonal antibody Ki-67. *J Immunol*. 1984; 133:1710-1715.

Gibbons R J. Review and discussion of the role of mucus in mucosal defense. In:Strober, W, Hanson, L, and Sell, K, ed. *Recent advances in mucosal immunity*. New York: Raven Press; 1982:343-351.

Gilbard J P, Rossi S R. Tear film and ocular surface changes in a rabbit model of neurotrophic keratitis. *Ophthalmol*. 1990; 97:308-312.

Gipson I K. Anatomy of the conjunctiva, cornea and limbus. In:Smolin, G, and Thoft, R, ed. *The Cornea*. Boston: Little, Brown and Co.; 1994:3-24.

Gipson I K, Tisdale A S. Visualization of conjunctival goblet cell actin cytoskeleton and mucin content in tissue whole mounts. *Exp Eye Res*. 1997; 65:407-415.

Greiner J V, Weidman T A, Korb D R, Allansmith M R. Histochemical analysis of secretion vesicles in nongoblet conjunctival epithelial cells. *Acta Ophthalmol*. 1985; 63.

Huang A J, Tseng S C, Kenyon K R. Morphogenesis of rat conjunctival goblet cells. *Invest Ophthalmol Vis Sci*. 1988; 29:969-975.

Inatomi T, Spurr-Michaud S J, Tisdale A S, Zhan Q, Feldman S T, Gipson I K. Expression of secretory mucin genes by human conjunctival epithelia. *Invest Ophthalmol Vis Sci*. 1996; 37:1684-1692.

Jeffery P K, Gaillard D, Maret S. Human airway secretory cells during development and in mature airway epithelium. *Eur Respir J*. 1992; 5:93-104.

Jumblatt M M, McKenzie R W, Jumblatt J E. MUC5AC mucin is a component of the human precorneal tear film. *Invest Ophthalmol Vis Sci*. 1999; 40:43-49.

Kaartinen L, Nettesheim P, Adler K B, Randell S H. Rat trachael epithelial cell differentation in vitro. *In Vitro Cell Dev Biol Anim*. 1993; 29A:481-492.

Kawano K, Uehara F, Sameshina M, Ohba N. Application of lectins for detection of goblet cell carbohydrates of the human conjunctiva. *Exp Eye Res*. 1984; 38:439-447.

Kessing S V. Investigations of the conjunctival mucin (quantitative studies of goblet cells of the conjunctiva). *Acta Ophthalmol*. 1968; 95: suppl. 1.

Kinoshita S, Kiorpes T C, Friend J, Thoft R A. Goblet cell density in ocular surface disease: a better indicator than tear mucin. *Arch Ophthalmol*. 1983; 101:1284-1287.

Krenzer K L, Freddo T F. Cytokeratin expression in normal human bulbar conjunctiva obtained by impression cytology. *Invest Ophthalmol Vis Sci*. 1997; 38:142-152.

Lamberts D W. Physiology of the tear film. In:Smolin, G, and Thoft, R, ed. *The Cornea*. Boston: Little, Brown and Co; 1994:439-483.

Latkovic S. The ultrastructure of the normal conjunctival epithelium of the guinea pig. III. The bulbar zone, the zone of the fornex and the suprandular zone. *Acta Ophthalmol*. 1979; 57:305-320.

Lemp M A, Holly F J, Iwata S, Dohlman C. The precorneal tear film. I. Factors in spreading and maintaining a continuous tear film over the corneal surface. *Arch Ophthalmol*. 1970; 83:89-94.

Lemp M A. The mucin-deficient dry eye. *Int Ophthalmol Clin*. 1973; 13:185-189.

Lemp M A. Basic principles and classification of dry eye disorders. In:Lemp, M, and Marquardt, R, ed. *The Dry Eye: A Comprehensive Guide*. Berin: Springer Verlag; 1992:101-132.

Moore C P, Wilsman N J, Nordheim E V, Majors L J, Collier L L. Density and distribution of canine conjunctival goblet cells. *Invest Ophthalmol Vis Sci*. 1987; 28:1925-1932.

Nichols B A, Chioppino M L, Dawson C R. Demonstration of the mucous layer of the tear film by electron microscopy. *Invest Ophthalmol Vis Sci*. 1985; 26:464-473.

Oduntan A O. The inferior conjunctiva of the monkey. *Acta Anat (Basel)*. 1992; 143:178-181.

Rheinwald J, Green H. Epidermal growth factor and the multiplication of cultured human epidermal keratocytes. *Nature*. 1977; 265:421-424.

Rios J D, Zoukhri D, Rawe I M, Hodges R R, Zieske J D, Dartt D A. Immunolocalization of muscarinic and VIP receptor subtypes and their role in stimulating goblet cell secretion. *Invest Ophthalmol Vis Sci*. 1999; 40:1102-1111.

Setzer P Y, Nichols B A, Dawson C R. Unusual structure of rat conjunctival epithelium. Light and electron microscopy. *Invest Ophthalmol Vis Sci*. 1987; 28:531-537.

Sheehan D C, Hrpchack B B (1980) Theory and Practice of Histochemistry, C V Mosby, St Louis.

Srinivasan B D, Worgul B V, Iwamoto T, Merriam G R. The conjunctival epithelium: II. Histochemical and ultrastructural studies on human and rat conjunctiva. *Ophthalmic Res*. 1997; 9:65-79.

Steuhl K P. Ultrastructure of the conjunctival epithelium. *Dev Ophthalmol*. 1989; 19:1-104.

Sun T, Green H. Cultured epithelial cells of cornea, conjunctiva andskin:absence of marked intrinsic divergence of their differentiated states. *Nature*. 1977; 269:489-493.

Towbin H, Staehelin T, Gordon J. Electrophoretic transfer of proteins from polyacrylamide gels to nitrocellulose sheets: procedures and some applications. *Proc Natl Acad Sci USA*. 1979; 76:4350-4354.

Tsai R J F, Tseng S C G. Substrate modulation of cultured rabbit conjunctival epithelial cells. *Invest Ophthalmol Vis Sci*. 1988; 29:1565-1576.

Tseng S C G, Hirst L, Maumenee A, Kenyon K R, Sun T T, Green W R. Possible mechanisms for the loss of goblet cells in mucin-deficient disorders. *Ophthalmol*. 1984; 91:545-552.

Tseng S C G, Hirst L W, Farazdaghi M, Green W R. Goblet cell density and vascularization during conjunctival trans-differentation. *Invest Ophthalmol Vis Sci*. 1984; 25:1168-1176.

Wei Z G, Wu R L, Lavker R M, Sun T T. In vitro growth and differentation of rabbit bulbar fornix and palpebral conjunctival epithelia. *Invest Ophthalmol Vis Sci*. 1993; 34:1814-1828.

Wu R, Nolan E, Turner C. Expression of trachael differentiated functions in serum-free hormone-supplemented medium. *J Cell Physiol*. 1985; 125:167-181.

Wu R, Martin W R, Robinson C B, A S G J, Plopper C G, Kurland G, Last J A, Cross C E, McDonald R J, Boucher R. Expression of mucin synthesis and secretion in human tracheobronchial epithelial cells grown in culture. *Am J Respir Cell Biol*. 1990; 3:467-478.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A mammalian goblet cell line that is immortalized, wherein goblet cells for said line are derived from a method of producing a culture of goblet cells comprising the steps of:
   (a) providing an explant of conjunctival mammalian tissue;
   (b) culturing said explant in a growth medium;
   (c) allowing said explant to grow until cell growth in the form of nodules is observed around said explant;
   (d) removing said explant, leaving said nodules in said growth medium;
   (e) allowing cells from said nodules to grow to form said culture of goblet cells; and
   (f) genetically engineering cells from said culture of goblet cells to form a culture of immortalized said goblet cells.

2. The goblet cell line of claim 1, wherein, in said method for deriving said cell line, said conjunctival mammalian tissue is from a human mammal.

3. The goblet cell line of claim 1, wherein, in said method for deriving said cell line, said conjunctival mammalian tissue comprises the fornical region.

4. The goblet cell line of claim 1, wherein, in said method for deriving said cell line, said conjunctival mammalian tissue comprises the nictitating membrane.

5. The goblet cell line of claim 1, wherein, in said method for deriving said cell line, said conjunctival mammalian tissue is from a mammal selected from the group consisting of human, rat, mouse, rabbit, cat, dog, sheep, goat, cow, and pig.

6. A kit for examining mucin from goblet cells comprising goblet cells according to claim 1 and instructions for use thereof.

* * * * *

UNITED STATES PATENT AND TRADEMARK OFFICE
CERTIFICATE OF CORRECTION

PATENT NO. : 7,316,927 B2 Page 1 of 1
APPLICATION NO. : 11/441890
DATED : January 8, 2008
INVENTOR(S) : Marie A. Shatos et al.

It is certified that error appears in the above-identified patent and that said Letters Patent is hereby corrected as shown below:

Column 13, line 24, "256" should read --25%--.

Signed and Sealed this

Thirteenth Day of July, 2010

David J. Kappos
*Director of the United States Patent and Trademark Office*